United States Patent [19]

Holtkamp

[11] Patent Number: Plant 5,627

[45] Date of Patent: Jan. 7, 1986

[54] AFRICAN VIOLET PLANT NAMED NEW ORLEANS

[75] Inventor: Reinhold Holtkamp, Isselburg, Fed. Rep. of Germany

[73] Assignee: Gessellschaftsvertrag uber die Erfindergemeinschaft "OPTIMARA", Rees Haffen, Fed. Rep. of Germany

[21] Appl. No.: 477,688

[22] Filed: Mar. 22, 1983

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named New Orleans having upright flower stems, large frilled flowers lilac in color, with a more intense dark lilac on the frilled margins, vigorous growth habit with early flowering, attractive girl type leaves, and non-dropping and long lasting flowers.

1 Drawing Figure

1

The present invention comprises a new and distinct cultivar of African violet plant, botanically known as *Saintpaulia ionantha,* and hereinafter referred to by the cultivar name New Orleans.

The new cultivar was referred to during the breeding and selection process by the designation G 9/IX girl, and is a product of a planned breeding program.

The new cultivar was originated from a cross made in a controlled breeding program in Isselburg, West Germany. The female, or seed parent was a cultivar designated d 150/2 red girl. The male, or pollen parent was a cultivar designated d 134/11 lilac frill.

The new cultivar New Orleans was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

New Orleans has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of New Orleans, which in combination distinguish this African violet as a new and distinct cultivar:

(1) Upright flower stems, 7–10 in number.

(2) Lilac frilled flowers, 6–10 per stem.

(3) The upper petals and flowers margins are intense dark lilac in color.

(4) Vigorous growth habit with early flowering.

(5) Large flowers.

(6) Attractive girl type leaves.

(7) Non-dropping, long lasting flowers.

New Orleans is very unique with regard to its overall characteristics, but is similar in flower color to Massachusetts, disclosed in my previously issued U.S. Plant Pat. No. 4,773.

2

The accompanying photographic drawing shows a typical specimen plant of the new cultivar. The colors appearing in the photograph are as true as possible with color illustrations of this type.

In the following description, color references are made to The Horticultural Colour Chart (HCC) issued by Wilson Colour Ltd., except where general colors of ordinary significance are referred to. Color values were taken under natural light conditions approximately midday in Nashville, Tenn.

Botanical classification: *Saintpaulia ionantha,* Ramat. cv New Orleans.

Parentage:

*Male parent.*—d 134/11 lilac frill.

*Female parent.*—d 150/2 red girl.

Propagation: The new cultivar holds its distinguishing characteristics through successive propagations by leaf cuttings and by division of shoots.

Plant: From 8 cm. to 10 cm. tall when grown in pots, and approximately 20 cm. in diameter when fully grown.

Leaves:

*General form.*—Round, heart shape.

*Diameter.*—6 cm. for mature leaves.

*Texture.*—Velvet soft.

*Aspect.*—Slightly shiny under, edges slightly serrated.

*Veins.*—Pronounced.

*Color (upperside).*—Parsley Green 00926/1.

*Color (underside).*—Sung Green 000658.

*Petiole.*—Reddish Green.

Flowers:

*Buds.*—Ball shape, 10 mm. before opening.

*Sepals.*—5 mm. long, spear shape. Color: Brownish-green. Calyx: Seed grown together with receptacle. Aspect: Flat. Peduncle: Erect and rigid.

*Individual flowers.*—Size: 45 mm. Color: Upperside: Violet 36/3, darker parts spectrum violet 735. Underside: Violet 36. Borne: Upright on short peduncle. Shape: Violet shape, frilled. Corolla: Compact flower bouquet, with the flowers being carried on 7–10 stems. Flowering time: 8–10 weeks after potting.

Reproductive organs:

*Anthers.*—Two, composed of four cells.

*Styles.*—Ovary is light green and hairy with purple base.

Roots: White when young and active, brownish when older.

Disease resistance: Good as known to date.

General observations: New Orleans is a very uniform growing variety with upright flower stems each carrying up to 10 or more flowers which are two-tone lilac in color and frilled on the margins. Flowers do not drop or dry off after full maturity. The flower head is full and compact centrally above the leaves.

I claim:

1. A new and distinct African violet plant named New Orleans, as described and illustrated, and particularly characterized by upright flower stems, large frilled flowers lilac in color, with a more intense dark lilac on the frilled margins, vigorous growth habit with early flowering, attractive girl type leaves, and non-dropping and long lasting flowers.

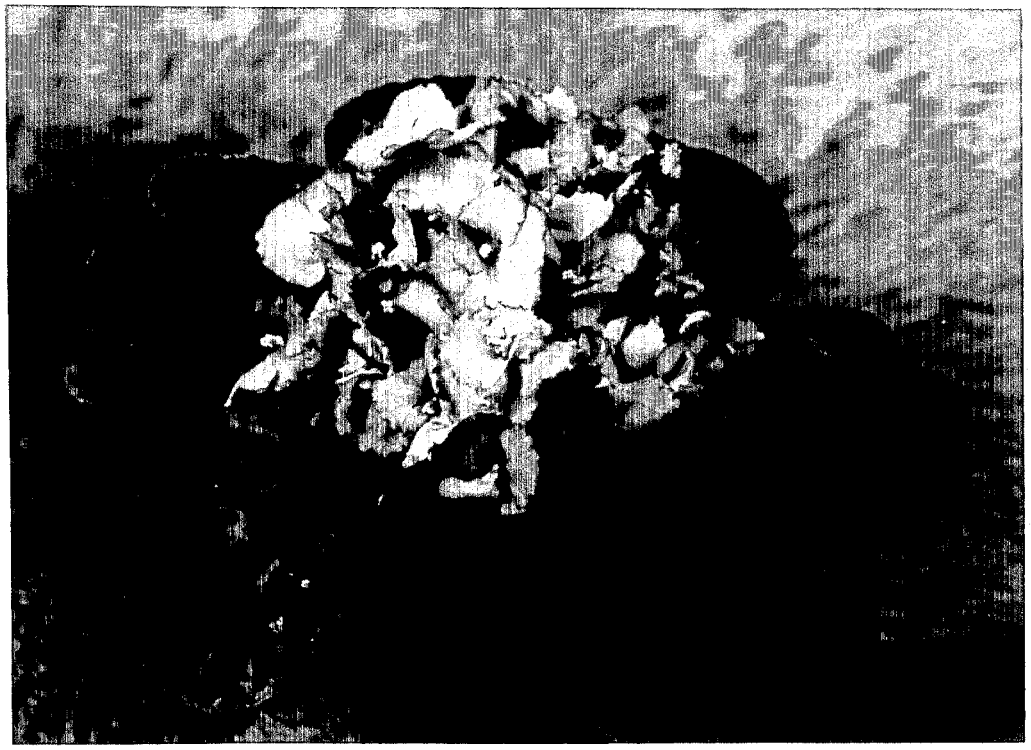

* * * * *